United States Patent
Fitzjarrell

[11] Patent Number: 5,759,559
[45] Date of Patent: Jun. 2, 1998

[54] METHOD AND COMPOSITION FOR TREATING ACNE

[76] Inventor: Edwin A. Fitzjarrell, 68994 N. Pine St., Sisters, Oreg. 97759

[21] Appl. No.: 841,764

[22] Filed: May 5, 1997

[51] Int. Cl.$^6$ ............................................. A61K 6/00
[52] U.S. Cl. ........................ 424/401; 424/195.1; 514/859
[58] Field of Search ........................ 424/401, 195.1; 514/859

[56] References Cited

U.S. PATENT DOCUMENTS

| | | | |
|---|---|---|---|
| 4,619,829 | 10/1986 | Motschan | 424/128 |
| 4,725,609 | 2/1988 | Kull, Jr. | 514/355 |
| 4,743,422 | 5/1988 | Raaf | 424/47 |
| 4,900,550 | 2/1990 | Lowry | 424/195.1 |
| 5,266,318 | 11/1993 | Taylor-McCord | 424/195.1 |
| 5,520,991 | 5/1996 | Eustatiu | 424/195.1 |

*Primary Examiner*—D. Gabrielle Brouillette

[57] ABSTRACT

A method and composition for treating outbreaks of acne. Initially, the acne affected area is cleaned. A topical spray comprising about 1 to 20 grams niacinamide per 100 grams solution in an inert carrier is then applied to the area. A composition that includes lysine, selenium, chromium and zinc and any desired vitamins and minerals is then taken orally in the form of a capsule or tablet. Generally, at least two spray applications are made and two capsules are taken each day. For optimum skin cleaning, an exfoliation scrub such as a conventional apricot facial scrub is applied to the skin prior to application of the niacinamide topical spray.

10 Claims, 1 Drawing Sheet

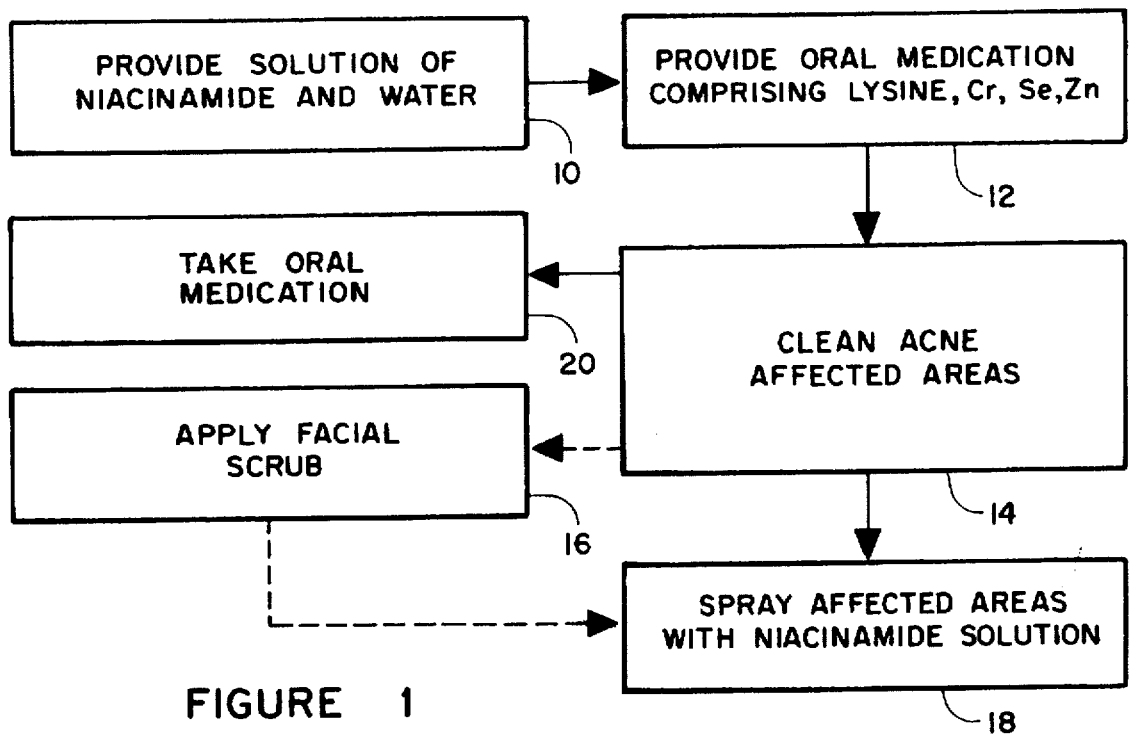
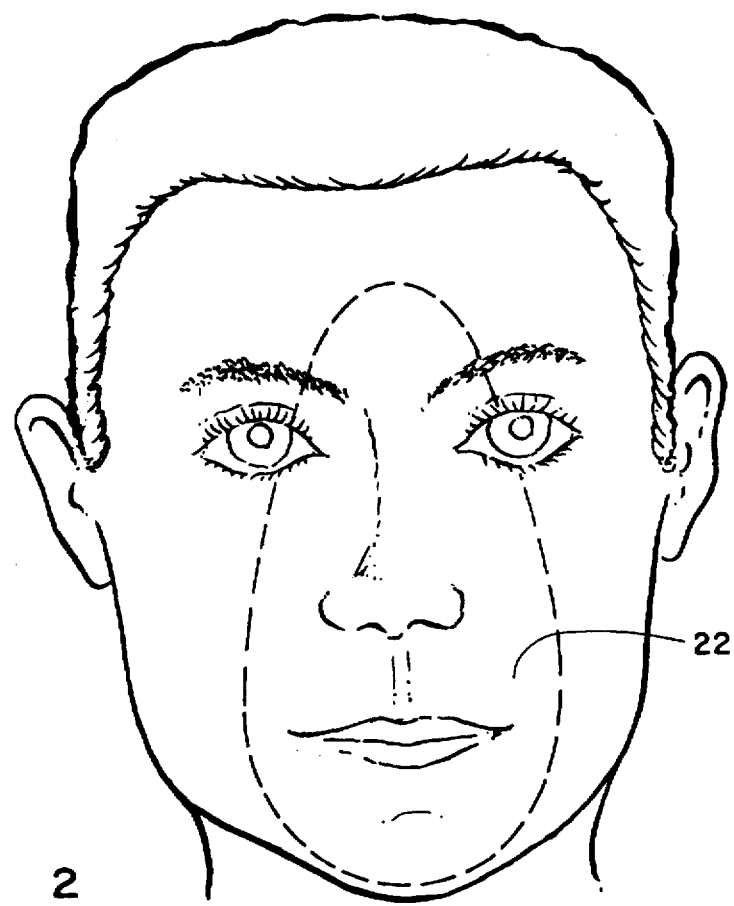

METHOD AND COMPOSITION FOR TREATING ACNE

FIELD OF THE INVENTION

This invention relates to methods and compositions for treating acne.

BACKGROUND OF THE INVENTION

Acne is a skin disorder that occurs most commonly among teen-agers. It consists of various kinds of blemishes on the face, upper chest and back. Severe acne can result in scarring. Acne is most likely in the facial area extending from around the nose to around the chin. This area is also most visible and acne here can be very distressing to the victim.

During early adolescence, hormone production begins that stimulates the oil glands in the skin. These sebaceous glands grow larger and produce more oil. Each sebaceous gland empties into a hair follicle and passes to the skin through a pore. Sometimes the pores become plugged and oil accumulates under the plugs. Pimples and cysts, caused by the acne bacillus, become infected resulting in redness and pus. Cysts may leave permanent scars, as may pimples if squeezed or scratched. Mild acne can be treated with diet changes, careful washing and nonprescription lotions containing benzoyl peroxide, topical creams containing salicylic acid, or other medications. Vitamin A palmitate may be applied topically for the treatment of acne and other skin disorders as described by Lerner in U.S. Pat. Nos. 5,556,887 and 5,520,919. Severe acne may be treated with tetracycline, 13-cis-retinoic acid and other prescription drugs. The skin may be treated with acid or freezing in some cases to make the skin peel. These treatments are often unsuccessful and may have significant side effects. Often, at best, these treatments reduce the intensity or frequency of acne outbreaks.

The most difficult area for treating acne is a generally "O" or elliptical shaped area on the face that includes the nose and chin. Acne can also occur on other parts of the face, the shoulders, neck, etc.

Thus, there is a continuing need for methods and compositions for treating acne that are more effective in preventing flare-up of acne and in reducing or eliminating acne outbreaks that have begun and that have fewer side effects.

SUMMARY OF THE INVENTION

The above-noted problems, and others, are overcome in accordance with this invention by a treatment method that includes a novel medicated topical spray and a unique oral supplement. The preferred method includes applying the spray to a clean face morning and evening and taking two capsules of the oral supplement daily. For optimum results, the skin is cleaned with an exfoliating scrub prior to applying the topical spray.

The spray comprises from about 1 to 20 volume percent niacinamide in a carrier, such as water. Mild cases of acne will respond well to the spray used alone. However, for most cases the combination of spray and oral supplement will provide best results. For severe outbreaks of acne that include pitting and pustules the exfoliating scrub should also be used in the treatment.

The oral supplement basically comprises lysine(HCL), selenium, zinc and chromium. For best results, multi-vitamins and other desirable agents are included, typically Vitamin A (Palmitate), thiamine HCL (B-1), riboflavin (B-2), niacinamide (B-3), pantothenic acid (B-5), cyanocobalamin (B-12), folic acid, biotin, ascorbic acid (Vitamin C), Vitamin D, Vitamin E (succinate) and Ascorbyl palmitate.

Any suitable scrub may be used when one is found desirable. Particularly effective scrubs include apricot facial scrubs of the sort available from Freeman and St. Ives.

It is, therefore, an object to provide an effective treatment for acne. Another object is to provide an easy and convenient treatment method for acne that is particularly effective in the facial "O-zone". A further object is to provide a treatment that reduces the incidence and severity of acne outbreaks.

BRIEF DESCRIPTION OF THE DRAWING

Details of the invention, and of preferred embodiments thereof, will be further understood upon reference to the drawing, wherein:

FIG. 1 is a flow diagram of the method of this invention; and

FIG. 2 is a schematic elevation view of a person's face showing the "O-zone".

DETAILED DESCRIPTION OF PREFERRED EMBODIMENTS

The steps in the method of this invention are set forth in the block diagram of FIG. 1.

The topical spray solution is prepared by mixing niacinamide with any suitable inert carrier, such as water, as indicated in Block 10. Any suitable ratio of niacinamide to carrier may be used. From about 1 to 20 volume percent niacinamide in the carrier has been found to be effective. Since the higher percentages, while very effective, tend to cause stinging and drying of the skin, it is preferred that from about 2 to 10 grams niacinamide per 100 grams solution be used for optimum over all results.

The oral medication is prepared, as indicated in Block 12 by mixing the various ingredients and preparing doses in suitable form, such as capsules, tablets or the like. Basically, the oral medication comprises lysine, chromium, zinc and selenium, plus any other suitable ingredients as desired. A typical daily dose would be from 1 to 6 capsules. Each capsule preferably comprises from about 400 to 700 mg lysine, about 0.5 to 0.7 mg chromium(GTF), about 2.5 to 4 mg selenium (selenite and or seleno methionine) and about 20 to 30 mg zinc (picolinate). Other vitamins and minerals may be included as desired. For best results, multi-vitamins are included.

An optimum formulation is as follows:

| INGREDIENTS | WT. PER BATCH in grams | WT. PER CAPSULE in mg |
|---|---|---|
| Lysine (HCl) | 2812.500 | 562.500 |
| Chromium (GTF) | 5.000 | 1.000 |
| Selenium (SeMet) | 16.667 | 3.333 |
| Selenium (Selenite) | 0.370 | 0.074 |
| Zinc (Picolinate) | 125.000 | 25.000 |
| Vitamin A (Palmitate) | 25.000 | 5.000 |
| Thiamine (HCl) (B-1) | 14.045 | 2.809 |
| Niacinamide (B-3) | 25.000 | 5.000 |
| Pantothenic Acid (B-5) | 27.174 | 5.435 |
| Pyridoxine (HCl) B-6 | 30.340 | 6.068 |
| Riboflavin (B-2) | 12.690 | 2.538 |
| Cyanocobalamin (B-12) | 0.125 | 0.025 |
| Folic Acid | 0.366 | 0.073 |
| Biotin | 0.250 | 0.050 |
| Vitamin C (Ascorbic Acid) | 225.000 | 45.000 |

-continued

| INGREDIENTS | WT. PER BATCH in grams | WT. PER CAPSULE in mg |
|---|---|---|
| Vitamin D | 0.040 | 0.080 |
| Vitamin E (Succinate) | 71.715 | 14.343 |
| Copper (Gluconate) | 18.519 | 3.704 |
| Ascorbyl Palmitate | 54.348 | 10.870 |

Prior to use of the topical solution, the area affected by acne is cleaned as indicated in Block 14. Any suitable cleaning method may be used, typically using a suitable cleaning agent and water. For best results, it is preferred that an exfoliation scrub, such as a conventional apricot facial scrub, be used to assure skin cleanliness and to lightly abrade the skin, as indicated in Block 16.

After the skin is cleansed, the topical solution is sprayed on the area as indicated in Block 18. In most cases, the central facial area or "O-zone" as indicated in FIG. 2, is most in need of treatment. Any suitable spraying device may be used, such as conventional pump or aerosol sprayers. Typically, the skin will be cleansed and sprayed at least twice a day. The total of said solution applied is preferably about 3 ml/day.

The oral medication is also taken as indicated in Block 20. Typically from 1 to 6 capsules may be taken each day with each capsule containing the quantities of the ingredients as described above. In most case, two capsules daily, takenwith meals, is sufficient. However, in severe cases up to 6 capsules may be taken daily for up to seven days.

As seen in FIG. 2, the most severe and difficult to treat acne occurs in the area delineated by line 22, an "O-zone" including the nose, upper lip and chin.

Use of the treatment method described will generally show positive results within about 21 days. The treatment should be begun at the first sign of acne.

While certain specific relationships, materials and other parameters have been detailed in the above description of preferred embodiments, those can be varied, where suitable, with similar results. Other applications, variations and ramifications of the present invention will occur to those skilled in the art upon reading the present disclosure. Those are intended to be included within the scope of this invention as defined in the appended claims.

I claim:

1. A method of treating acne, which comprises:
   providing a solution comprising from about 1 to 20 volume per cent niacinamide in an inert carrier liquid;
   providing an oral medication each dose of which comprises about 200 to 700 mg lysine, about 2.5 to 4 mg selenium in a form selected from seleno methionine and selenites, about 20 to 30 mg zinc in picolinate form and about 0.5 to 0.7 mg chromium in picolinate form;
   cleaning an acne affected area of skin;
   spraying said acne affected area with said solution; and
   taking at least one dose of said oral medication each day.

2. The method according to claim 1 wherein from 2 to 6 of said doses are swallowed each day.

3. The method according to claim 1 including the further step of cleaning said acne affected area with an apricot facial scrub.

4. The method according to claim 1 wherein up to about 1000 ml of said solution is sprayed onto the acne affected skin area each day.

5. The method according to claim 1 including the step of mixing into said oral medication at least one ingredient selected from the group consisting of Vitamin A, Thiamine, Niacinamide, Pantothenic Acid, Pyridoxine, Riboflavin, Cyanocobalamin, Folic Acid, Biotin, Vitamin C, Vitamin D, Vitamin E, Copper, Ascorbyl Palmitate.

6. The method according to claim 1 wherein said inert carrier liquid is water.

7. A kit for use in treating acne, which comprises:
   means for cleaning a skin area affected by acne;
   spray means for applying a liquid solution on said skin area;
   said spray means containing a quantity of a solution comprising from about 1 to 20 grams niacinamide per 100 grams solution in an inert carrier liquid; and
   individual doses of an oral medication comprising about 200 to 700 mg lysine, about 2.5 to 4 mg selenium, about 20 to 30 mg zinc and about 0.5 to 0.7 mg chromium.

8. The kit according to claim 7 said oral medication further includes at least one ingredient selected from the group consisting of Vitamin A, Thiamine, Niacinamide, Pantothenic Acid, Pyridoxine, Riboflavin, Cyanocobalamin, Folic Acid, Biotin, Vitamin C, Vitamin D, Vitamin E, Copper and Ascorbyl Palmitate.

9. The kit according to claim 7 wherein said inert carrier liquid is water.

10. The kit according to claim 7 wherein said means for cleaning the skin includes an apricot facial scrub.

* * * * *